US010736936B2

(12) United States Patent
Stern et al.

(10) Patent No.: US 10,736,936 B2
(45) Date of Patent: Aug. 11, 2020

(54) THERAPEUTIC METHODS USING CYCLOSPORINE COMPONENTS

(71) Applicant: Allergan, Inc., Irvine, CA (US)

(72) Inventors: Michael E. Stern, Mission Viejo, CA (US); David Power, San Clemente, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 15/284,281

(22) Filed: Oct. 3, 2016

(65) Prior Publication Data
US 2017/0020954 A1 Jan. 26, 2017

Related U.S. Application Data

(60) Continuation of application No. 11/479,481, filed on Jun. 30, 2006, now Pat. No. 9,457,060, which is a division of application No. 10/990,055, filed on Nov. 15, 2004, now Pat. No. 7,151,085.

(51) Int. Cl.
A61K 38/00 (2006.01)
A61K 38/13 (2006.01)
A61K 9/00 (2006.01)

(52) U.S. Cl.
CPC ............ A61K 38/13 (2013.01); A61K 9/0014 (2013.01); A61K 9/0034 (2013.01); A61K 9/0053 (2013.01)

(58) Field of Classification Search
None
See application file for complete search history.

(56) References Cited

U.S. PATENT DOCUMENTS

| 3,278,447 A | 10/1966 | McNicholas |
| 4,388,307 A | 6/1983 | Cavanak |
| 4,614,736 A | 9/1986 | Delevallee et al. |
| 4,649,047 A | 3/1987 | Kaswan |
| 4,814,323 A | 3/1989 | Andrieu et al. |
| 4,839,342 A | 6/1989 | Kaswan |
| 4,970,076 A | 11/1990 | Horrobin |
| 4,990,337 A | 2/1991 | Kurihara et al. |
| 4,996,193 A | 2/1991 | Hewitt et al. |
| 5,286,730 A | 2/1994 | Caufield et al. |
| 5,286,731 A | 2/1994 | Caufield et al. |
| 5,342,625 A | 8/1994 | Hauer et al. |
| 5,368,854 A | 11/1994 | Rennick |
| 5,411,952 A | 5/1995 | Kaswan |
| 5,474,979 A | 12/1995 | Ding et al. |
| 5,504,068 A | 4/1996 | Komiya et al. |
| 5,540,931 A | 7/1996 | Hewitt et al. |
| 5,719,123 A | 2/1998 | Morley et al. |
| 5,739,105 A | 4/1998 | Kim et al. |
| 5,807,820 A | 9/1998 | Elias et al. |
| 5,843,452 A | 12/1998 | Wiedmann et al. |
| 5,843,891 A | 12/1998 | Sherman |
| 5,858,401 A | 1/1999 | Bhalani et al. |
| 5,866,159 A | 2/1999 | Hauer et al. |
| 5,891,846 A | 4/1999 | Ishida et al. |
| 5,916,589 A | 6/1999 | Hauer et al. |
| 5,951,971 A | 9/1999 | Kawashima et al. |
| 5,962,017 A | 10/1999 | Hauer et al. |
| 5,981,479 A | 11/1999 | Ko et al. |
| 5,981,607 A | 11/1999 | Ding et al. |
| 5,998,365 A | 12/1999 | Sherman |
| 6,008,191 A | 12/1999 | Singh |
| 6,008,192 A | 12/1999 | Al-Razzak et al. |
| 6,022,852 A | 2/2000 | Klokkers et al. |
| 6,024,978 A | 2/2000 | Hauer et al. |
| 6,046,163 A | 4/2000 | Stuchlik et al. |
| 6,159,933 A | 12/2000 | Sherman |
| 6,254,860 B1 | 7/2001 | Garst |
| 6,323,204 B1 | 11/2001 | Burke |
| 6,346,511 B1 | 2/2002 | Singh et al. |
| 6,350,442 B2 | 2/2002 | Garst |
| 6,413,547 B1 | 7/2002 | Bennett et al. |
| 6,420,355 B2 | 7/2002 | Richter et al. |
| 6,468,968 B2 | 10/2002 | Cavanak et al. |
| 6,486,124 B2 | 11/2002 | Olbrich et al. |
| 2001/0014665 A1 | 8/2001 | Fischer et al. |
| 2003/0021816 A1 | 1/2003 | Kang et al. |
| 2003/0044452 A1 | 3/2003 | Ueno |
| 2003/0055028 A1 | 3/2003 | Stergiopoulos et al. |
| 2003/0060402 A1 | 3/2003 | Cavanak et al. |
| 2003/0087813 A1 | 5/2003 | Or et al. |

(Continued)

FOREIGN PATENT DOCUMENTS

| DE | 19810655 | 9/1999 |
| WO | 2003-030834 | 4/2003 |
| WO | 2003051385 A1 | 6/2003 |

OTHER PUBLICATIONS

Shirazi, Mucins in inflammatory bowel disease, Postgrad Med. J. 2000, 76, 473-478.*
Winter et al. Cyclosporine Enemas for distal Pouchitis, Gastroenterology Unit, The Radcliffe Infirmary, 1992.*
McColl et al. British Medical Bulletin 1998: 54 (1).*
Medical Dictionary; analog and derivative, accessed 2018.*
Rudinger et al. Peptide Hormones, JA Parsons, Ed. (1976), pp. 1-7.*
Smilek et al. Proc. Natl. Acad. Sci. USA (1991) 88, pp. 9633-9637.*
Acheampong, Andrew et al, Distribution of Cyclosporin A in Ocular Tissues After Topical Administration to Albino Rabbits and Beagle Dogs, Current Eye Research, 1999, 91-103, 18(2).

(Continued)

Primary Examiner — Jeanette M Lieb
(74) Attorney, Agent, or Firm — Lorenz Siddiqi

(57) ABSTRACT

Methods of treating humans or animals having various conditions are disclosed which include administering a cyclosporine component. Among the conditions treated are dry mouth syndrome, verruciform xanthoma, achlorhydria, mucous cysts, oral submucous fibrosis, oral nevi, cancer of the oral mucosa, maloplakia of the genito-urinary tract, vulvovaginitis, helicobacter pylori infection, duodenal ulcers, peptic ulcers, conditions affecting the uterus and appendicitis.

4 Claims, No Drawings

(56) References Cited

U.S. PATENT DOCUMENTS

| | | |
|---|---|---|
| 2003/0104992 A1 | 6/2003 | Or et al. |
| 2003/0109425 A1 | 6/2003 | Or et al. |
| 2003/0109426 A1 | 6/2003 | Or et al. |
| 2003/0143250 A1 | 7/2003 | Hauer et al. |
| 2005/0106189 A1 | 5/2005 | Wohlrab et al. |

OTHER PUBLICATIONS

Acheampong, Andrew, et al., Cyclosporine Distribution into the Conjunctiva, Cornea, Lacrimal Gland, and Systemic Blood Following Topical Dosing of Cyclosporine to Rabbit, Dog, and Human Eyes, Lacrimal Gland, Tear film, and Dry Eye Syndromes 2—Basic Science and Clinical Relevance, Adv. Exp. Med. Biol., Plenum Press, New York, 1998, vol. 438, 1001-1004.
Akpek, Esen Karamursel et al, A Randomized Trial of Topical Cyclosporin 0.05% in Topical Steroid-Resistant Atopic Keratoconjunctivitis, Ophthalmology, 2004, 476-482, 111.
Angelov, O. et al, Preclinical Safety Studies of Cyclosporine Ophthalmic Emulsion, Adv Exp Med Biol, 1998, 991-995, 438.
Ardizzone, Sandro et al, A Practical Guide to the Management of Distal Ulcerative Colitis, Drugs, 1998, 519-542, 55(4).
Banic, Marko et al, Effect of Cyclosporine in a Murine Model of Experimental Colitis, Digestive Diseases and Sciences, Jun. 2002, 1362-1368, 47(6).
Brewster, Marcus et al, Enhanced Delivery of Ganciclovir to the Brain Through the Use of Redox Targeting, Antimicrobial Agents and Chemotherapy, Apr. 1994, 817-823, 38(4).
Brewster, Marcus et al, Intravenous and Oral Pharmacokinetic Evaluation of a 2-Hydroxypropyl-ß-cyclodextrin-Based Formulation of Carbamazepine in the Dog: Comparison with Commercially Available Tablets and Suspensions, Journal of Pharmaceutical Sciences, Mar. 1997, 335-339, 86(3).
Brewster, Marcus et al, Preparation, Characterization, and Anesthetic Properties of 2-Hydroxypropyl-ß-cyclodextrin Complexes of Pregnanolone and Pregnenolone in Rat and Mouse, Journal of Pharmaceutical Sciences, Oct. 1995, 1154-1159, 84(10).
Brinkmeier, Thomas et al, Pyodermatitis-Pyostomatitis Vegetans: A Clinical Course of Two Decades with Response to Cyclosporine and Low-Dose Prednisolone, Acta Derm Venereol, 2001, 134-136, 81.
Corfield, et al., Mucins and mucosal protection in the gastrointestinal tract: New prospects for mucins in the pathology of gastrointestinal disease, Gut, 2000, 589-594, vol. 47, Issue 4, BMJ Publishing Group, London.
Dorlands, Dorland's Medical Dictionary, Dorland's Illustrated Medical Dictionary, 1994, 6 Pages, 28th Edition, W.B. Saunders Company.
Drewe, et al., The absorption site of cyclosporin in the human gastrointestinal tract, British Journal of Clinical Pharmacology, Jan. 1992, 39-43, vol. 33, No. 1.
Drosos, A. A. et al, Efficacy and Safety of Cyclosporine-A Therapy for Primary Sjogren's Syndrome, Ter. Arkh., 1998, 77-80, 60(4).
Drosos, A.A. et al, Cyclosporin A Therapy in Patients with Primary Sjogren's Syndrome: Results at One Year, Scand J Rheumatology, 1986, 246-249, 61.
Eisen, Drore et al, Topical Cyclosporine for Oral Mucosal Disorders, J Am Acad Dermatol, Dec. 1990, 1259-1264, 23.
Epstein, Joel et al, Topical Cyclosporine in a Bioadhesive for Treatment of Oral Lichenoid Muscosal Reactions, Oral Surg Oral Med Oral Pathol Oral, 1996, 532-536, 82.
Erdmann, S. et al, Pemphigus Vulgaris Der Mund—Und Kehlkopfschleimhaut Pemphigus Vulgaris of the Oral Mucosa and the Larynx, H+G Zeitschrift Fuer Hautkrankheiten, 1997, 283-286, 72(4).
Gaeta, G.M. et al, Cyclosporin Bioadhesive Gel in the Topical Treatment of Erosive Oral Lichen Planus, International Journal of Immunopathology and Pharmacology, 1994, 125-132, 7(2).
Gipson, Ilene et al, Character of Ocular Surface Mucins and Their Alteration in Dry Eye Disease, The Ocular Surface Apr. 2004, 131-148, 2(2).
Gremse, David et al, Ulcerative Colitis in Children, Pediatr Drugs, 2002, 807-815, 4(12).
Gunduz, Kaan et al, Topical Cyclosporin Treatment of Keratoconjunctivitis Sicca in Secondary Sjogren's Syndrome, Acta Ophthalmologica, 1994, 438-442, 72.
Isaac, et al., Production of Cyclosporins by Tolypocladium Niveum Strains, Antimicrobial Agents and Chemotherapy, Jan. 1990, 121-127, vol. 34, No. 1, American Society for Microbiology.
Lopatin, D.E., Chemical Compositions and Functions of Saliva, Aug. 24, 2001, 31 Pages.
Morris, Raymond G., Cyclosporine Therapeutic Drug Monitoring—an Established Service Revisited, Clinical Biochemist Reviews, May 2003, 33-46, vol. 24, Australian Association of Clinical Biochemists.
Pedersen, Anne Marie et al, Primary Sjogren's Syndrome: Oral Aspects on Pathogenesis, Diagnostic Criteria, Clinical Features and Approaches for Therapy, Expert Opin Pharma, 2001, 1415-1436, 2(9).
Phillips, Thomas et al, Cyclosporine Has a Direct Effect on the Differentiation of a Mucin-Secreting Cell Line, Journal of Cellular Physiology, 2000, 400-408, 184.
Present, D.H. et al, Cyclosporine and Other Immunosuppressive Agents: Current and Future Role in the Treatment of Inflammatory Bowel Disease, American Journal of Gastroenterology, 1993, 627-630, 88(5).
Robinson, N. A. et al, Desquamative Gingivitis: A Sign of Mucocutaneous Disorders—a Review, Australian Dental Journal, 2003, 205-211, 48(4).
Rudinger, J., Characteristics of the amino acids as components of a peptide hormone sequence, Peptide Hormones, 1976, 1-7, JA Parsons, Ed.
Sall, Kenneth et al, Two Multicenter, Randomized Studies of the Efficacy and Safety of Cyclosporine Ophthalmic Emulsion in Moderate to Severe Dry Eye Disease, Ophthalmology, 2000, 631-639, 107.
Sandborn, William et al, A Placebo-Controlled Trial of Cyclosporine Enemas for Mildly to Moderately Active Left-Sided Ulcerative Colitis, Gastroenterology, 1994, 1429-1435, 106.
Sandborn, William et al, Cyclosporine Enemas for Treatment-Resistant, Mildly to Moderately Active, Left-Sided Ulcerative Colitis, American Journal of Gastroenterology, 1993, 640-645, 88(5).
Schwab, Matthias et al, Pharmacokinetic Considerations in the Treatment of Inflammatory Bowel Disease, Clin Pharm, 2001, 723-751, 60(10).
Small, David et al, Blood Concentrations of Cyclosporin A During Long-Term Treatment With Cyclosporin A ophthalmic Emulsions in Patients with Moderate to Severe Dry Eye Disease, Journal of Ocular Pharmacology and Therapeutics, 2002, 411-418, 18(5).
Smilek, Dawn et al, A Single Amino Acid Change in a Myelin Basic Protein Peptide Confers the Capacity to Prevent Rather Than Induce Experimental Autoimmune Encephalomyelitis, Proc. Natl. Acad. Sci., Nov. 1991, 9633-9637, 88.
Spiryda, et al., Graft-versus-Host Disease of the Vulva and/or Vagina: Diagnosis and Treatment, Biology of Blood and Marrow Transplantation, 2003, 760-765, vol. 9, American Society for Blood and Marrow Transplantation.
Stevenson, Dara et al, Efficacy and Safety of Cyclosporin A ophthalmic Emulsion in the Treatment of Moderate-to-Severe Dry Eye Disease, Ophthalmology, 2000, 967-974, 107.
The Online Medical Dictionary, Derivative, Analog, Analogue, Xerostomia, accessed Jul. 7, 2005 and Jul. 13, 2005, 6 Pages.
Tsubota, Kazuo et al, Use of Topical Cyclosporin A in a Primary Sjogren's Syndrome Mouse Model, Invest Ophthalmol Vis Sci, Aug. 1998, 1551-1559, 39(9).
Van Der Reijden, Willy et al, Treatment of Oral Dryness Related Complaints (Xerostomia) in Sjogren's Syndrome, Ann Rheum Dis, 1999, 465-473, 58.

(56) References Cited

OTHER PUBLICATIONS

Winter, T.A. et al, Cyclosporin A Retention Enemas in Refractory Distal Ulcerative Colitis and 'Pouchitis', Scand J Gastroenterol, 1993, 701-704, 28.

\* cited by examiner

THERAPEUTIC METHODS USING CYCLOSPORINE COMPONENTS

RELATED APPLICATION

This is a continuation of U.S. patent application Ser. No. 11/479,481 filed on Jun. 30, 2006, which is a division of U.S. patent application Ser. No. 10/990,055 filed on Nov. 15, 2004, the entire disclosure of both applications is incorporated by reference herein.

The present invention relates to methods of providing desired therapeutic effects to humans or animals using compositions including cyclosporine components. More particularly, the invention relates to methods including administering to dysfunctional or mucin deficient mucosal tissue of a human or animal a therapeutically effective amount of a cyclosporine component to provide a desired therapeutic effect to the mucosal tissue. The invention also relates to treating the uterus of a female human or animal. In addition, the present invention relates to treating appendicitis in a human or animal.

The use of cyclosporin-A and cyclosporin A derivatives to treat ophthalmic conditions has been the subject of various patents, for example Ding et al U.S. Pat. No. 5,474,979; Garst U.S. Pat. No. 6,254,860; and Garst U.S. Pat. No. 6,350,442, this disclosure of each of which is incorporated in its entirely herein by reference.

In addition, a number of prior art patents have disclosed the use of cyclosporine, administered topically and/or systemically, as a treatment for other conditions and/or diseases.

Mucosal tissue, in general, forms the lining of many conduits or vessels in the body of a human or animal. In many instances, if a medication is topically applied to such a conduit or vessel to treat a condition/disease of the tissue underlying the mucosal tissue, the medication is required to penetrate or pass through the mucosal tissue to provide a therapeutically effective amount of the medication to the mucosal tissue. Several patents have disclosed cyclosporine-containing compositions which are useful in penetrating mucosal tissue to provide treatment to the underlying tissue. These patents include: Stuchlik et al U.S. Pat. No. 6,046,163; and Al-Razzak et al U.S. Pat. No. 6,008,192.

However, mucosal tissue itself is subject to various conditions and diseases which adversely affect the functioning of such tissue, and ultimately adversely affect the human or animal. For example, the mucosal tissue of a human or animal may be mucin deficient, which is often manifested in a degree of dryness, and can cause irritation, discomfort and/or pain to the human or animal. Various conditions, for example and without limitation, verruciform xanthoma of the skin, verruciform xanthoma in the genito-urinary tract, achlorhydria, mucous cysts, oral submucous fibrosis, oral nevi, cancers of the oral cavity, maloplakia of the genito-urinary tract, helicobacter plylori infections, duodenal ulcers, peptic ulcers, and a number of conditions of the female uterus and genito-urinary tract, may be, at least in part, caused by and/or result in dysfunctional mucosal tissue.

Appendicitis is a condition which is often painful, or even substantially debilitating, to a human or animal.

It would be advantageous to provide methods of treating dysfunctional mucosal tissue. Further, it would be advantageous to provide methods for treating appendicitis in a human or animal, and one or more conditions of the uterus of a female or animal.

SUMMARY OF THE INVENTION

New methods of treating dysfunctional mucosal tissue of a human or animal, conditions of the uterus of a female human or animal and appendicitis in a human or animal have been discovered. The present methods provide substantial overall efficacy in providing the desired therapeutic effect or effects. In addition, other important benefits are obtained employing the present methods. For example, the present methods can be easily and effectively practiced by the prescribing physician and patient without causing substantial or undue patient stress. In short, the present methods provide substantial and acceptable overall efficacy, together with other advantages, such as ease of practice and reduced patient stress.

In one aspect of the present invention, the present methods comprise administering a therapeutically effective amount of a cyclosporine component to mucosal tissue of a human or animal having a mucin deficiency. The mucosal tissue is located in a part of the human or animal selected from an oral cavity, a genito-urinary tract and a gastrointestinal tract. The administering step is effective in treating the mucin deficiency.

In another aspect of the invention, the present methods comprise topically administering a therapeutically effective amount of a cyclosporine component to dysfunctional mucosal tissue of a human or animal. The mucosal tissue is located in a part of the human or animal selected from an oral cavity, a genito-urinary tract and a gastrointestinal tract. The administering step is effective in treating the dysfunctional mucosal tissue.

In a further aspect of the invention, the present methods comprise administering a therapeutically effective amount of a cyclosporine component to a human female or an animal female to treat a condition affecting a uterus, for example, affecting mucosal tissue of a uterus, of the female, the administering being effective in treating the condition.

In an additional aspect of the invention, the present methods comprise administering a therapeutically effective amount of a cyclosporine component to a human or animal having appendicitis, thereby treating the appendicitis.

Each and every feature described herein, and each and every combination of two or more of such features, is included within the scope of the present invention provided that the features included in such a combination are not mutually inconsistent.

These and other aspects and advantages of the present invention are apparent in the following detailed description, examples and claims.

DETAILED DESCRIPTION

The present methods employ cyclosporine components to treat humans or animals, for example, other mammals, afflicted with various conditions. Among the conditions treated in accordance with the present invention are those involving dysfunctional mucosal tissue of the oral cavity, genito-urinary tract and gastrointestinal tract of the human or animal. Other conditions treated in the present invention include conditions affecting the uterus of a female human or animal, and appendicitis in the human or animal.

In general, the present methods comprise administering a therapeutically effective amount of a cyclosporine component to a human or animal having a condition to be treated. The term "condition" as used herein includes, without limitation, one or more injuries, diseases, illnesses, other conditions and the like. The administering step is effective to treat the condition. A condition is treated in accordance with the present invention when, for example and without limitation, as a result of the present administering step, one or more symptoms of the condition is reduced in severity or eliminated, the progression of the condition is slowed or stopped or reversed, the condition itself is reduced in severity or substantially (or totally) resolved and the like therapeutic benefits.

In one embodiment, the present administering step comprises topically administering the cyclosporine component to the affected area, for example, the affected mucosal tissue, of the human or animal. Topical administration allows a therapeutically effective amount of the cyclosporine component to be administered to treat a condition, without subjecting the remainder of the human or animal to the cyclosporine component.

Employing reduced systemic or blood concentrations of cyclosporine component, as in one embodiment of the present invention, is advantageously effective to treat the condition/disease under treatment, preferably with substantially no detectable concentration of the cyclosporine component in the blood of the human or animal being treated. The cyclosporine component concentration of blood can be advantageously measured using a validated liquid chromatography/mass spectrometry-mass spectrometry (VLC/MS-MS) analytical method, such as described elsewhere herein.

In one embodiment, in the present methods the blood of the human or animal has concentrations of cyclosporine component of 0.1 ng/ml or less. Any suitable condition caused by or resulting in dysfunctional mucosal tissue may be treated in accordance with the present invention. In one embodiment, the mucosal tissue has a mucin deficiency which at least in part results in the human or animal having a condition selected from the group consisting of dry mouth syndrome, verruciform xanthoma, achlorhydria, mucous cysts, oral submucous fibrosis, oral nevi, maloplakia of the genito-urinary tract, helicobacter pylori infection, duodenal ulcers and peptic ulcers.

Dry mouth syndrome may be the result at least in part of at least one of mucin deficiency and immune inflammation salivary gland secretion variation. The use of cyclosporine components in accordance with the present invention is effective in treating dry mouth syndrome resulting at least in part from one or both of mucin deficiency and immune inflammation salivary gland secretion.

Examples of conditions of the uterus or female genito-irinary tract which may be treated in accordance with the present invention include, without limitation, salpingitis, cervicitis, and endometriosis.

In accordance with the present invention, a cyclosporine component may be administered to a human or animal having appendicitis to treat the appendicitis.

In one embodiment, the cyclosporine component may be administered to a human or animal as part of the combination treatment to treat a condition of the human or animal. For example, the cyclosporine component may be administered to the human or animal along with one or more other therapeutic agents effective in treating the condition of the human or animal. The other therapeutic agent or agents can be administered to the human or animal in the same composition with the cyclosporine component or in a different composition from the cyclosporine component. Examples of useful other therapeutic components include, without limitation, antibiotics, various pain medications, anti-inflammatory medications and the like and mixtures thereof.

Alternatively, or in addition, the cyclosporine component may be administered to a human or animal in conjunction with, for example, prior to, during and/or after, one or more surgical procedures to treat the condition. Such administration of the cyclosporine component may facilitate the surgical procedure(s), for example, and without limitation, by controlling and/or otherwise treating the condition prior to the procedure(s), by making the procedure(s) easier to tolerate and/or less stressful during the procedure(s), and by reducing recovery time and/or enhancing extent of recovery from the surgical procedure(s) after the procedure(s).

Any suitable cyclosporine component effective in the present methods may be used.

Cyclosporines are a group of nonpolar cyclic oligopeptides with known immunosuppressant activity. Cyclosporin A, along with several other minor metabolites, as well as cyclosporin B, C, D, E, F, G, H, I, J, K, L, M, N, O, P, Q, R, S, T, U, V, W, X, Y and Z, have been identified. In addition, derivatives, salts and the like of such cyclosporines and a number of synthetic analogs have been prepared and may be useful in the present invention. See, for example, the Garst Patents noted elsewhere herein.

In general, commercially available cyclosporines may contain a mixture of several individual cyclosporines which all share a cyclic peptide structure consisting of eleven amino acid residues with a total molecular weight of about 1,200, but with different substituents or configurations of some of the amino acids.

The term "cyclosporine component" as used herein is intended to include any individual member of the cyclosporine group, salts thereof, derivatives thereof, analogs thereof and mixtures thereof, as well as mixtures of two or more individual cyclosporines salts thereof, derivatives thereof, analogs thereof and mixtures thereof.

Particularly preferred cyclosporine components include, without limitation, cyclosporin A, derivatives of cyclosporin A, salts of cyclosporin A and the like and mixtures thereof. Cyclosporin A is an especially useful cyclosporine component.

The chemical structure for cyclosporin A is represented by Formula 1

Formula I

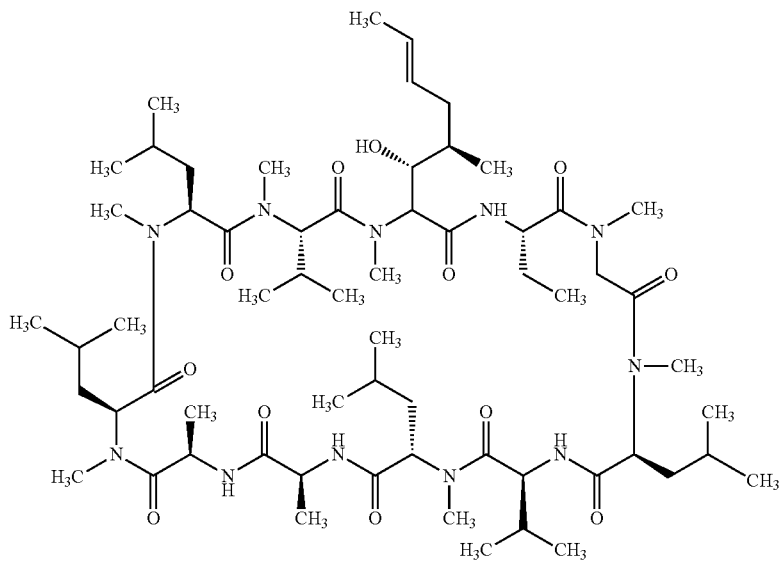

As used herein the term "derivatives" of a cyclosporine refer to compounds having structures sufficiently similar to the cyclosporine so as to function in a manner substantially similar to or substantially identical to the cyclosporine, for example, cyclosporin A, in the present methods. Included, without limitation, within the useful cyclosporin A derivatives are those selected from ((R)-methylthio-Sar)$^3$-(4'-hydroxy-MeLeu) cyclosporin A, ((R)-(Cyclo)alkylthio-Sar)$^3$-(4'-hydroxy-MeLeu)$^4$-cyclosporin A, and ((R)-(Cyclo)alkylthio-Sar)$^3$-cyclosporin A derivatives described below.

These cyclosporine derivatives are represented by the following general formulas (II), (III), and (IV) respectively:

Formula II

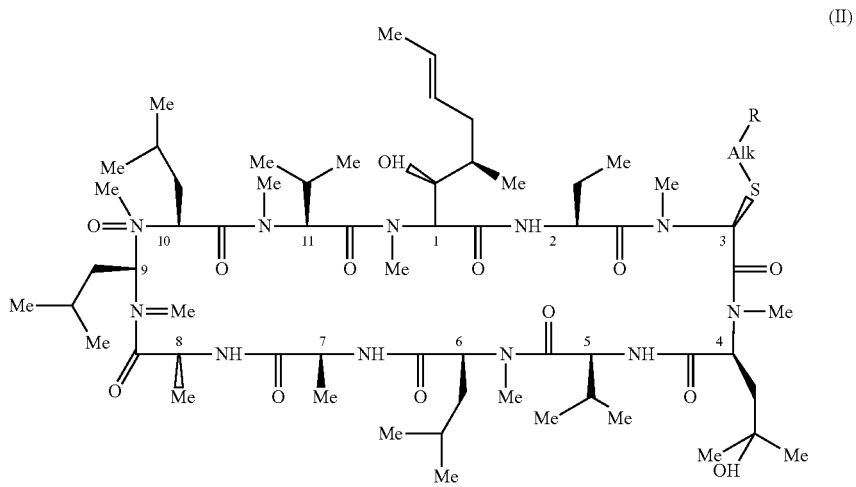

(II)

Formula III

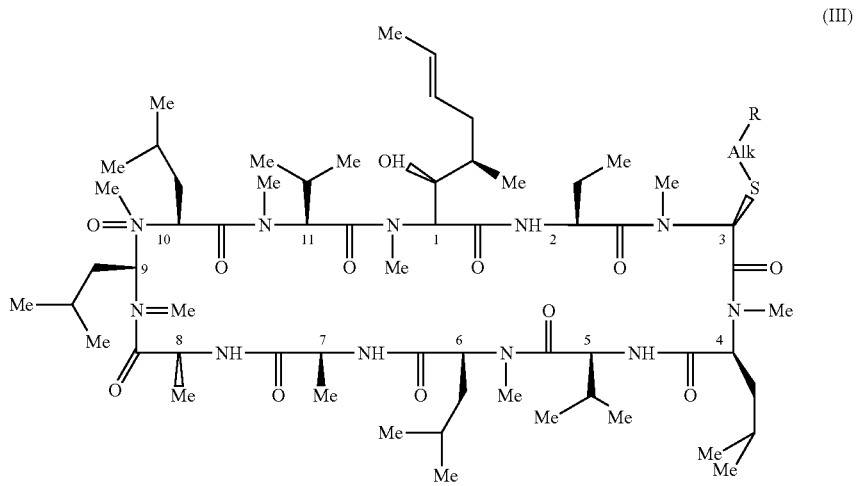

(III)

Formula IV

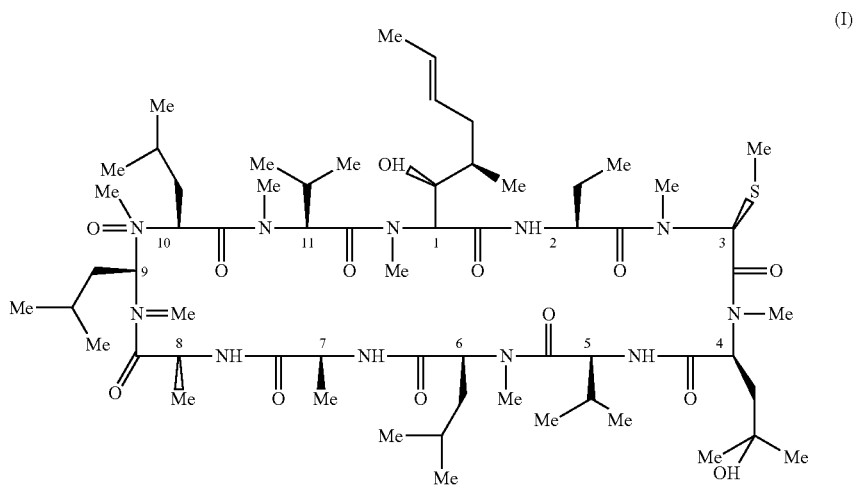

(I)

wherein Me is methyl; Alk is 2-6C alkylene or 3-6C cycloalkylene; R is OH, COOH, alkoxycarbonyl, —NR$_1$R$_2$ or N(R$_3$)—(CH$_2$)—NR$_1$R$_2$; wherein R$_1$,R$_2$ is H, alkyl, 3-6C cycloalkyl, phenyl (optionally substituted by halo, alkoxy, alkoxycarbonyl, amino, alkylamino or dialkylamino), benzyl or saturated or unsaturated heterocyclyl having 5 or 6 members and 1-3 heteroatoms; or NR$_1$R$_2$ is a 5 or 6 membered heterocycle which may contain a further N, O or S heteroatom and may be alkylated; R$_3$ is H or alkyl and n is 2-4; and the alkyl moieties contain 1-4C.

The present methods may be practiced employing any suitable compositions or combinations of compositions including therapeutically effective amounts of cyclosporine component. The cyclosporine component is present in an amount effective to provide the desired therapeutic effect when the cyclosporine-containing composition is administered to a human or animal in accordance with the present invention. The cyclosporine component advantageously is present in the compositions in amounts ranging from about 0.03% to about 15% or about 20% or more by weight of the composition. In one embodiment, the cyclosporine component is present in an amount of about 0.1% to about 5% or about 10% or about 15% by weight of the composition. It is intended, however, that the choice of a particular amount of cyclosporine component is to be made in accordance with factors well known in the medicinal arts, including mode of administration, the size and condition of the human or animal and the type and severity of the condition to be treated.

The presently useful compositions may be liquids, suspensions, emulsions, semi-solids, capsules, gels, lotions, creams and the like. Those skilled in the art of pharmaceutical formulation are able to formulate suitable compositions including cyclosporine components in a suitable form, such as those forms noted herein, for example, including one or more pharmaceutically acceptable excipients, such as those conventionally used in similar compositions. Of course, care should be taken to use composition components which are compatible with the cyclosporin component being used and which do not unduly or significantly interfere with the administering step in which the composition is being used or with the human or animal being treated.

For example, cyclosporine components can be combined with carriers which form emulsions upon mixing with water. Such emulsions are described, for example, and without limitation, in Cavanak U.S. Pat. No. 4,388,307, the disclosure of which is hereby incorporated in its entirety herein by reference. Carriers, for example, and without limitation, glyceride carriers, may assist in alleviating problems of physical instability such as precipitation of the cyclosporine component from solution, and may also enable higher blood plasma concentrations, if desired.

In a useful embodiment, the presently useful compositions include hydrophobic components. Any suitable hydrophobic component may be employed in the present invention. Advantageously, the cyclosporine component is solubilized in the hydrophobic component. In one embodiment, the hydrophobic component may be considered as comprising a discontinuous phase in the presently useful cyclosporine component-containing compositions, for example, oil-in-water emulsions.

The hydrophobic component may be present in an effective amount, for example, in an amount of up to about 1.0% by weight or about 1.5% by weight or more of the composition.

Preferably, the hydrophobic component comprises one or more oily materials. Examples of useful oil materials include, without limitation, vegetable oils, animal oils, mineral oils, synthetic oils and the like and mixtures thereof. In a very useful embodiment, the hydrophobic component comprises one or more higher fatty acid glycerides. Excellent results are obtained when the hydrophobic component comprises castor oil.

Other useful cyclosporine component-containing compositions comprise the cyclosporine component in admixture with an emulsifying amount of a fatty acid glyceride, such as castor oil and the like, and a surfactant, such as polysorbate 80. Such compositions are described in Ding et al U.S. Pat. No. 5,474,979, the disclosure which is hereby incorporated in its entirety herein by reference. Also see Kaswan U.S. Pat. No. 4,649,047 and Kaswan U.S. Pat. No. 5,411,952, the disclosure of each of which is hereby incorporated in its entirety herein by reference.

In one embodiment, the presently useful compositions are self-emulsifying which, when exposed to an aqueous medium, form fine oil-in-water emulsions with little or no agitation. The property of self-emulsification permits such formulations to be administered in concentrated form, as for example in a hard gelatin or soft elastic capsules, with the expectation that a fine emulsion will be formed in the digestive tract. Additionally, emulsions may be prepared by combining a self-emulsifying pre-concentrate with an aqueous medium.

Previously-disclosed self-emulsifying systems include those in which a cyclosporine component is combined with mixtures of (i) medium-chain triglycerides and nonionic surfactants, (ii) vegetable oils and partial glycerides, such as polyglycolized glycerides or medium-chain mono- and diglycerides, or (iii) vegetable oils and nonionic surfactants such as polysorbate 80 or PEG-25 glyceryl trioleate.

In certain self-emulsifying formulations, a "microemulsion preconcentrate" of a cyclosporine component is formed by combining the cyclosporine component with (I) a hydrophilic phase, (II) a lipophilic phase, and (III) a surfactant, as well as optional thickeners, antioxidants or other excipients. Examples of such compositions are disclosed in Hauer et al U.S. Pat. No. 5,342,625, the disclosure which is hereby incorporated in its entirety herein by reference.

In addition, suitable compositions may include cyclosporine components in combination with a hydrophilic solvent phase and one or more surfactants, but not containing lipophilic solvents. Such cyclosporine component-containing formulations may be stable, simple to prepare, and have good pharmacokinetic properties.

As used herein, the terms "binary system", "binary composition" and "binary system of excipients" denote those cyclosporine component-containing formulations and compositions which contain, in addition to the cyclosporine component, a combination of at least one hydrophilic solvent and at least one surfactant, but which lack a lipophilic solvent. Such compositions may be supplemented with additional adjuvants and still be considered "binary", so long as they do not include a lipophilic solvent phase.

To prepare such pharmaceutical compositions, a binary system is combined with a cyclosporine component. The hydrophilic phase may comprise one or more of the known pharmaceutically acceptable hydrophilic solvents or excipients that are capable of solubilizing the cyclosporine component. Suitable classes of hydrophilic compounds include, for example and without limitation, pharmaceutically acceptable alcohols including the polyethylene glycols.

Examples of hydrophilic phase components useful in the presently useful compositions include, but are not limited to, water, ethanol, benzyl alcohol, propylene glycol, low molecular weight polyethylene glycols having a molecular weight of up to about 1,000, glycol, dimethyl isosorbide and the like and mixtures thereof.

The compositions may be prepared as semi-solids and placed into hard gelatin rather than soft elastic capsules, to allow for the use of ethanol and similar solvents.

The hydrophilic phase, comprising one or more hydrophilic solvents, typically comprises about 10% to about 90% by weight of the pharmaceutical composition. The precise amount used will vary depending on the nature of the hydrophilic compound or compounds used, the amount of cyclosporine component present, the dosage form, the condition being treated and other factors known in the art. Preferably the hydrophilic phase comprises about 20% to about 80%, and more preferably about 30% to about 60%, by weight of the composition. Where non-aqueous hydrophilic components are used, water can be included in the formulation at levels varying from about 0.5% to about 10%, or preferably from about 1% to about 5%, based on total weight of the composition.

Any of the known pharmaceutically acceptable surfactants may be used, including nonionic, anionic, cationic, and combinations thereof. Nonionic surfactants are preferred, and especially those surfactants having a hydrophile/lipophile balance (HLB) of 10 or more. Alternatively, certain combinations of high- and low-HLB surfactants may be utilized; preferably, such mixed surfactants are used in ratio such that the aggregate surfactant HLB (when weighted according to proportions used) remains in excess of 10.

Examples of suitable surfactants include, but are not limited to, polyoxyethylene derivatives of natural or hydrogenated vegetable oils such as castor oil; polyoxyethylene-sorbitan fatty acid esters, such as mono-, di- and tri-lauryl, palmityl, stearyl and oleyl esters; alkyl/dialykyl sulfate, sulfonate or sulfosuccinate salts such as sodium lauryl sulfate and dioctyl sodium sulfosuccinate; polyoxyethylene fatty acid esters; phospholipids such as lecithins; transesterification products of natural vegetable oil triglycerides and polyalkylene polyols; sorbitan fatty acid esters; pentaerythritol fatty acid esters; polyoxyethylene glycol alkyl ethers and esters; and the like. The surfactants may be used alone or in combination.

Examples of specific surfactants which may be used include, without limitation, polyoxyethylene castor oil derivatives, such as polyoxyethylene glycerol triricinoleate polyoxyl 35 castor oil (CREMOPHOR® EL, available from BASF Corporation), and polyoxyl 40 hydrogenated castor oil (CREMOPHOR® RH40, available from BASF Corporation); mono-fatty acid esters of poloxyethylene (20) sorbitan, such as polyoxyethylene (20) sorbitan monooleate (TWEEN® 80), polyoxyethylene (20) sorbitan monostearate (TWEEN® 60), polyoxyethylene (20) sorbitan monopalmitate (TWEEN® 40), and polyoxyethylene (20) sorbitan monolaurate (TWEEN® 20) (all available from ICI Surfactants, Wilmington, Del.); polyoxyethylene glycol 200 monostearate (MYRJ® 52, available from Calgene Chemicals, Skokie, Ill.); polyglycerol esters with a HLB of 10 or greater, such as decablyceryl mono- and dioleate and the like; and mixtures thereof.

In some instances (as when the compositions are prepared as semi-solids), it may be advantageous to use at least one additional low-HLB surfactant along with one or more of the above high-HLB surfactant. Examples of low-HLB auxiliary surfactants which may be used include, but are not limited to, polyglycerol oleates (such as CAPROL® 10G40); lecithins; glyceryl monooleate or monolinoleate mixtures (such as MYVEROL® 18-99 or 18-92); propylene glycol laurate; and sorbitan oleates such as sorbitan monooleate (SPAN® 80), sorbitan trioleate (SPAN® 85), and sorbitan sesquioleate (SPAN® 20) (all available from ICI Surfactants, Wilmington, Del.). The surfactant phase may comprise about 10% to 90% by weight of the composition. Preferably the surfactant comprises about 20% to about 70% of the composition, and more preferably about 40% to about 60%, by weight.

If desired, the presently useful compositions may additionally comprise other pharmaceutically acceptable excipients, such as tonicity components, buffer components, polyelectrolyte components, thickeners, fillers, diluents, flavoring agents, coloring agents, antioxidants, preservatives, such as antibacterial or antifungal agents, acids and/or basis to adjust pH, and the like and mixtures thereof. Such additives, if present, may typically comprise about 0.01% to about 10% by weight of the composition. Such additives include those additives which are conventional and/or well known for use in similar pharmaceutical compositions. For example, suitable thickening agents include any of those known in the art, as for example pharmaceutically acceptable polymers and/or inorganic thickeners. Such agents include, but are not limited to, polyacrylate homo- and co-polymers; celluloses and cellulose derivatives; polyvinyl pyrrolidones; polyvinyl resins; silicates; and the like and mixtures thereof.

When desired, the cyclosporine-containing compositions may be prepared as semi-solid rather than liquid formulations by addition a greater proportion of appropriate thickening or solidifying agents. As noted above, such preparations may be particularly useful as fills for hard gelatin (as opposed to soft gelatin) capsules. Solidifiers suitable for the preparation of semi-solid compositions include, but are not limited to, polyethylene glycols having a molecular weight of more than about 1,000, such as PEG 1450 and PEG 3350; stearyl alcohol; and colloidal silicon dioxide (CAB-O-SIL® M-5, available from Cabot, Tuscola, Ill.). A semi-solid state may be often obtained by adding between about 8% or about 10% and about 15% or about 25% by weight solidifying agent. The actual amount of solidifying agent needed will depend on the physical characteristics of the other excipients which are present.

Except as otherwise noted elsewhere herein, the cyclosporine component-containing compositions may be administered topically and/or systemically, for example, by any of the methods known in the art. Such methods include, but are not limited to, systemic administration methods, for example, oral administration of a suspension formed by mixing a cyclosporine component-containing composition with an aqueous medium such as water, milk or juice; a cyclosporine component-containing composition placed in a soft elastic or hard gelatin capsule; parenteral administration including intravenous, intramuscular, intraperitoneal, intrasternal, subcutaneous and intraarticular injection or infusion of a cyclosporine component-containing composition; and/or topical administration methods, such as topical administration of ointments, drops, solutions, suspensions or emulsions including a cyclosporine component. Topical formulations, intended for administration to the skin or mucosa, may be prepared directly, or by combining a cyclosporine component-containing concentrate with a diluent, for example, an aqueous diluent. Such topical formulations may include additional excipients as necessary, for example, to modify consistency of the rate of absorption of the cyclosporine component.

In preparing the presently useful compositions, the components may be combined in any order with mixing or light agitation to ensure complete blending.

The cyclosporine component may be administered in a sufficient amount, and for a sufficient time, as required to provide the desired therapeutic effect. The specific therapeutically effective dosage level may be dependent on a number of factors including the specific condition to be treated, the severity of the condition, the activity of the particular cyclosporine component being employed, the specific cyclosporine component-containing composition employed, the time and method of administration, the duration of treatment, and other factors which are well known in the medical arts.

The following non-limiting examples illustrate certain aspects of the present invention.

Example 1

A male patient, age 30, suffering from dry mouth syndrome is treated with a flavored oral rinse in the form of an emulsion containing 0.2% by weight of cyclosporin A in a castor oil/water-containing carrier. This treatment is repeated three times daily for a week. After this period of treatment, the patient reports a reduction in at least one symptom of the dry mouth syndrome.

Example 2

A female patient, age 55, presents with a zerruciform xanthoma lesion of the oral mucosa. The patient is treated with a flavored oral rinse in the form of an emulsion comprising 0.2% by weight of cyclosporin A in a castor oil/water-containing carrier. This treatment is repeated twice daily for a month. After this time of treatment, the lesion has been reduced in size.

Example 3

A male patient, age 45, is found to have achlorhydria, which has progressed in severity over a period of time. In other words, the patient has been found to be producing a reduced amount of gastric acid. The patient is treated by drinking 20 ml of a flavored composition including 0.3% by weight of cyclosporin A in a castor oil/water-containing carrier. This treatment is repeated before each meal for 2 months. The patient reports experiencing reduced symptoms of the achlorhydia after this treatment.

Example 4

A female patient, age 30, is diagnosed with a mucus cyst in her mouth. The cyst is painful. The patient is treated with a flavored oral rinse as recited in Example 1. This treatment occurs 3 times daily for a week. After this period of treatment, the patient reports that the cyst is substantially eradicated.

Example 5

A male patient, age 30, suffering from oral submucous fibrosis syndrome is treated with a flavored oral rinse in the form of an emulsion containing 0.2% by weight of cyclosporin A in a castor oil/water-containing carrier. This treatment is repeated three times daily for two months. After this period of treatment, the patient reports a reduction in at least one symptom of the oral submucous fibrosis.

Example 6

A female patient, age 55, is diagnosed with mucosal melanocytic nevi in the oral cavity. The patient is treated with a flavored oral rinse in the form of an emulsion comprising 0.2% by weight of cyclosporin A in a castor oil/water-containing carrier. This treatment is repeated twice daily for a month. After this time of treatment, the condition is less severe than before treatment.

Example 7

A male patient, age 60, is found to have a cancer of the oral mucosa. The patient is treated with a flavored composition including 0.3% by weight of cyclosporin A in a castor oil/water-containing carrier. This treatment is repeated twice daily for 2 months. After this treatment, the progress of the cancer is substantially stopped. The patient reports experiencing less or reduced symptoms from the condition after this treatment. Surgical excision of the cancer may be undertaken.

Example 8

A female patient, age 30, is diagnosed with vulvovaginitis. The patient is treated by applying a topical cream containing 0.2% by weight of cyclosporin A in a conventional cream base to the affected area. This treatment occurs 2 times daily for a week. After this period of treatment, the patient reports that the severity of her condition has been lessened.

Example 9

A male patient, age 50, is suffering from a peptic ulcer in his stomach. The patient is treated by drinking 10 ml of a flavored composition containing 0.3% by weight of cyclosporin A in an aqueous carrier. This treatment is repeated three times daily for two months. In addition, during this period, the patient takes an effective amount of an antimicrobial medication to resolve the helicobacter pylori infection, if any that may be present. After this period of treatment, the patient reports a substantial reduction in at least one symptom of the peptic ulcer.

Example 10

A female patient, age 25, is diagnosed with salpingitis. The patient is treated with a pelvic lavage comprising 0.1% by weight of cyclosporin A in an aqueous carrier. This treatment is repeated once a week for a month. After this time of treatment, the condition has been substantially eliminated.

Example 11

A female patient, age 30, is found to have cervicitis. The patient is treated by applying a topical cream containing 0.2% by weight of cyclosporin A in a conventional cream base to the affected area. This treatment is repeated daily for two weeks. The patient reports experiencing less inflammation from the condition after this treatment.

Example 12

A female patient, age 30, is diagnosed with endometriosis. The patient is treated with a pelvic lavage comprising 0.1% by weight of cyclosporin A in an aqueous-based carrier. This treatment is repeated once after two weeks. In addition, the patient receives a conventional medication to facilitate reducing the size of the endometriosis cysts. After this two week period of treatment, the patient reports reduced pain from her condition.

Example 13

A male patient, age 30, suffering from appendicitis is treated with a composition containing 0.3% by weight of cyclosporin A in a conventional carrier. The composition was administered in the form of a rectal suppository three times daily for a week. In addition, during this time, a therapeutically effective amount of a conventional antibiotic is orally administered to the patient. After this period of treatment, the patient's appendicitis is effectively managed and he reports experiencing reduced or no pain.

While this invention has been described with respect to various specific examples and embodiments, it is to be understood that the invention is not limited thereto and that it can be variously practiced within the scope of the following claims.

What is claimed is:

1. A method of treating a mucin deficiency of mucosal tissue, the method comprising:
    drinking a liquid comprising cyclosporine A; thereby administering a therapeutically effective amount of the cyclosporine A to mucosal tissue of a human or animal having a mucin deficiency, the mucosal tissue being located in a part of a gastrointestinal tract in the human or animal, the administering step being effective in treating the mucin deficiency.

2. The method of claim 1 wherein the mucin deficiency at least in part results in the human or animal having a condition selected from the group consisting of achlorhydria, mucous cysts, submucous fibrosis, cancers of the mucosa, helicobacter pylori infection, duodenal ulcers, and peptic ulcers.

3. A method of treating dysfunctional mucosal tissue, the method comprising:
    drinking a liquid comprising cyclosporine, thereby administering a therapeutically effective amount of the cyclosporine to dysfunctional mucosal tissue of a human or animal, the mucosal tissue being located in a part of a gastrointestinal tract in the human or animal, the administering step being effective in treating the dysfunctional mucosal tissue.

4. The method of claim 3 wherein the dysfunctional mucosal tissue at least in part results in the human or animal having a condition selected from the group consisting of achlorhydria, mucous cysts, submucous fibrosis, cancers of the mucosa, helicobacter pylori infection, duodenal ulcers, and peptic ulcers.

\* \* \* \* \*